(12) United States Patent
Sakuma et al.

(10) Patent No.: US 9,339,452 B2
(45) Date of Patent: May 17, 2016

(54) HIGH INTERNAL WATER PHASE WATER-IN-OIL EMULSIFIED COSMETIC AND COSMETIC LIQUID APPLICATOR

(71) Applicant: MITSUBISHI PENCIL COMPANY, LIMITED, Shinagawa-ku (JP)

(72) Inventors: Satoshi Sakuma, Fujioka (JP); Nobuyuki Nakajima, Fujioka (JP); Susumu Suzuki, Fujioka (JP); Hiroaki Koyama, Shinagawa-ku (JP); Yuusuke Kyogoku, Fujioka (JP); Yukako Shinmura, Fujioka (JP)

(73) Assignee: MITSUBISHI PENCIL COMPANY, LIMITED, Tokyo (JP)

( * ) Notice: Subject to any disclaimer, the term of this patent is extended or adjusted under 35 U.S.C. 154(b) by 225 days.

(21) Appl. No.: 13/921,403

(22) Filed: Jun. 19, 2013

(65) Prior Publication Data

US 2013/0343801 A1  Dec. 26, 2013

(30) Foreign Application Priority Data

Jun. 22, 2012  (JP) .................................. 2012-140884
Jun. 22, 2012  (JP) .................................. 2012-141240
Jun. 10, 2013  (JP) .................................. 2013-122061

(51) Int. Cl.
*B43K 5/06* (2006.01)
*A61K 8/891* (2006.01)
(Continued)

(52) U.S. Cl.
CPC ................ *A61K 8/891* (2013.01); *A45D 40/26* (2013.01); *A61K 8/064* (2013.01); *A61K 8/894* (2013.01); *A61Q 19/00* (2013.01); *A61K 2800/10* (2013.01)

(58) Field of Classification Search
CPC ........ A61K 8/891; A61Q 19/00; A45D 40/26
USPC ..................................... 401/171–175; 424/63
See application file for complete search history.

(56) References Cited

U.S. PATENT DOCUMENTS 5,015,469 A * 5/1991 Yoneyama et al. ............. 424/59
5,216,033 A * 6/1993 Pereira et al. ................... 514/63
6,132,739 A * 10/2000 Leverett ....................... 424/401
(Continued)

FOREIGN PATENT DOCUMENTS

JP           3-79669 A     4/1991
JP       2001-220311 A    8/2001
(Continued)

*Primary Examiner* — Jennifer C Chiang

(74) *Attorney, Agent, or Firm* — Buchanan, Ingersoll & Rooney PC

(57) ABSTRACT

A high internal water phase water-in-oil emulsified cosmetic in which, in a system formed of an oil phase including silicone elastomer, polydimethylsiloxane and polyether modified silicone and a water phase including water in an amount of 60% or greater by mass. The water phase, at least, including one nonionic surfactant having an HLB value of 14 or greater, selected from a group consisting of polyoxyalkylene alkyl ethers, polyglycerin fatty acid esters, polyoxyalkylene glycerin fatty acid esters and polyalkyleneglycol fatty acid esters, in an amount of 0.03 to 0.6% by mass, is blended with pigments including an organic pigment, in an amount of 0.05 to 8% by mass. The viscosity at the shear rate of 3.83 sec$^{-1}$ at 25° C. is 1 to 100 Pa·sec, as well as an applicator with an applying part having a surface roughness Ra of 3 to 300 μm to store the cosmetic.

9 Claims, 2 Drawing Sheets

(51) Int. Cl.
   *A61Q 19/00* (2006.01)
   *A45D 40/26* (2006.01)
   *A61K 8/894* (2006.01)
   *A61K 8/06* (2006.01)

(56) References Cited

U.S. PATENT DOCUMENTS

| | | | |
|---|---|---|---|
| 6,548,074 B1 * | 4/2003 | Mohammadi | 424/401 |
| 8,579,533 B2 * | 11/2013 | Sasada et al. | 401/265 |
| 2010/0112017 A1 * | 5/2010 | Mizutani et al. | 424/401 |

FOREIGN PATENT DOCUMENTS

| | | |
|---|---|---|
| JP | 2003-81757 A | 3/2003 |
| JP | 2007-130157 A | 5/2007 |
| JP | 2007-236529 A | 9/2007 |
| JP | 2007-319392 A | 12/2007 |
| JP | 2008-212282 A | 9/2008 |
| JP | 2010-42046 A | 2/2010 |
| JP | 2010-100590 A | 5/2010 |
| JP | 2011-201824 A | 10/2011 |
| JP | 2012-72081 A | 4/2012 |

* cited by examiner

HIGH INTERNAL WATER PHASE WATER-IN-OIL EMULSIFIED COSMETIC AND COSMETIC LIQUID APPLICATOR

BACKGROUND OF THE INVENTION

1. Field of the Invention

The present invention relates to a high internal water phase water-in-oil emulsified cosmetic having water resistance and producing a fresh and light touch as well as relating an applicator suited to the cosmetic. More detailedly, the present invention relates to a high internal water phase water-in-oil emulsified cosmetic which is excellent in aging stability and brilliant in color, as well as relating to a liquid applicator which dispenses an application liquid such as a cosmetic, being viscous by nature, to an applying part so that the liquid is directly applied to the skin and which is suited to applying a cosmetic that is patted and spread on the skin.

2. Description of the Related Art

Since a water-in-oil emulsion composition presents a good affinity for the skin and prevents evaporation of moisture by covering the skin surface with an oil coating so as to protect the skin from drying and provide a skin treatment effect on the skin, the emulsion composition has been conventionally used as skin care cosmetics because of these properties. Further, since the water-in-oil emulsion composition is excellent in water repellency and is unlikely to cause deteriorating the makeup, it has been widely used for cosmetics such as makeup cosmetics and bases of medicines (see Patent Document 1, for example).

However, such emulsions have an oily component as the external phase, so that there have been problems with usability such as stickiness in use, poor spreadability, and hardness.

To deal with, there has been proposed a high internal water phase water-in-oil emulsified cosmetic which, presenting a fresh and light touch, despite of a water-in-oil type emulsion, has a content of a water phase component of 50.0% by mass (see Patent Document 2, for example).

Generally, in the case of water-in-oil emulsions, hydrophobically modified pigments such as, for example silicone or organofluoro resin treated pigments are used (see Patent Documents 3, 4, and 5, for example). Also in the case of high internal water phase water-in-oil emulsions, hydrophobically modified inorganic pigments are used (see Patent Document 2, for example).

However, since the ratio of the oil phase to the water phase is small in a high internal water phase water-in-oil emulsion so that there is a problem in stability when pigments and others are blended in the oil phase, hence it is necessary to use silicone modified coal-tar dyes (see Patent Document 6, for example). Usually, such a surface modification is done for inorganic pigments, and if the treatment with coal-tar dyes is also carried out using commonly the same equipment for the treatment with inorganic pigments, an enormous number of steps are necessary to wash the equipment to prevent contamination. Or, provision of another apparatus requires a large expenditure for investment, resulting in high cost.

For these reasons, some high internal water phase water-in-oil emulsions have been used as uncolored liquids such as milk lotions and skin creams, or others have been applied to no more than the category of foundations in which inorganic pigments are blended. Hence, there has been no composition available for point makeup using organic pigments.

As for cosmetic applicators having an applying part other than brushes, applicators that have a dispensing port in a spatula-shaped applying part and apply and spread the dispensed cosmetic by the applying part (see Patent Documents 7 to 9 of the applicants hereof, for example) as well as applicators that apply and spread a cosmetic using a smooth plane of a small area around a dispensing port (see Patent Documents 10 and 11 of the applicants hereof, for example), have been known.

In the case where the spatula-shaped applying part of each of the applicators disclosed in the above patent documents 7 to 9 is used to apply and spread a viscous liquid, no problem will occur when the cosmetic liquid is applied with some thickness as used for makeup like a lipstick. However, when the liquid has to be applied and spread thinly like a blusher, there occurs a problem that it requires a skill to put blush on the cheek without leaving traces of the spatula.

Further, in a case where a smooth applying part of a small area as in each of the applicators disclosed in above patent documents 4 and 5 is used to apply and spread a liquid, the liquid is liable to rope when the applying part departs from the skin, if the liquid is viscose. Hence there is a high risk of the thick part of application remaining on the skin, which also poses the problem that thin application requires a skill.

In particular, application and spreading of the liquid by patting is effective to apply a viscous blusher liquid thinly. However, under the present condition there occurs the problem that patting application using the applying part of any of applicators disclosed in above patent documents 7 to 11 only produces the imprint like multiple stamping, forming uneven coating.

[Patent Document 1] Japanese Patent Application Laid-open No. H03-79669 (claims, description and others)
[Patent Document 2] Japanese Patent No. 3782914 (claims, description, examples and others)
[Patent Document 3] Japanese Patent Application Laid-open No. 2012-72081 (claims, description and others)
[Patent Document 4] Japanese Patent Application Laid-open No. 2011-201824 (claims, description and others)
[Patent Document 5] Japanese Patent Application Laid-open No. 2010-100590 (claims, description and others)
[Patent Document 6] Japanese Patent Application Laid-open 2003-81757 (examples and others)
[Patent Document 7] Japanese Patent Application Laid-open No. 2007-319392 (claims, FIG. 2 and others)
[Patent Document 8] Japanese Patent Application Laid-open No. 2007-130157 (claims, FIG. 3 and others)
[Patent Document 9] Japanese Patent Application Laid-open No. 2007-236529 (claims, FIG. 8 and others)
[Patent Document 10] Japanese Patent Application Laid-open No. 2008-212282 (claims, FIG. 2 and others)
[Patent Document 11] Japanese Patent Application Laid-open No. 2010-42046 (claims, FIG. 2 and others)

SUMMARY OF THE INVENTION

In view of problems of the relating art and the status quo, the present invention is aimed at solving above problems, and the inventors hereof have tried to develop an inexpensive high internal water phase water-in-oil emulsified cosmetic, especially a cream blusher, which is highly stable and brilliant colors by blending pigments including organic pigments without any surface treatment into the water phase that occupies a relatively large proportion compared to the oil phase. Also, the object of the present invention is to provide a liquid applicator suitable for such as viscous cosmetic, which dispenses a viscous application liquid such as a cosmetic fluid by nature, to an applying part and enables the liquid to be directly applied and spread onto the skin by patting.

In order to stably disperse an organic pigment into the water phase, if the pigment is poor in solubility or dispersibility in water, it is necessary to enhance these factors. In some cases, the solubility of the organic pigment in the water phase and/or the oil phase may be rather made lower in order to make the cosmetics hard to deteriorate. When a conventional surface treatment as described above is implemented on a pigment to make the pigment dissolve or disperse into the oil phase, increase in cost not only is inevitable but surface treatment itself will degrade the property of being difficult for the makeup to deteriorate. Further, if the solubility of a pigment into both the water and oil phase is poor, it is advantageous that the pigment is blended and dispersed into the water phase side than the oil phase side, which is smaller in proportion.

Means for Solving the Problems

Under these circumstances, the inventors hereof have earnestly investigated and resultantly found out that use of a nonionic surfactant having specific physical properties makes it possible to stably disperse organic pigments into the water phase. The inventors hereof also found out that, in a liquid applicator comprising: an applying part fixed at the front end part of a barrel body for applying an application liquid by being put into contact with a target part; a thrusting mechanism arranged in the rear of the barrel body; a dispensing port for dispensing the application liquid to the applying part; and a communication passage formed to connect between the dispensing port and a reservoir, to push the application liquid from the reservoir to the dispensing port via the communication passage of the applying part by means of the thrusting mechanism and dispense the liquid from the dispensing port, if the applying surface of the applying part is specified so as to have particular physical properties, the liquid applicator for achieving the above object can be obtained.

That is, the present invention resides in the following (1) to (9).

(1) A high internal water phase water-in-oil emulsified cosmetic, wherein in a system formed of an oil phase including silicone elastomer, polydimethylsiloxane and polyether modified silicone and a water phase including water in an amount of 60% or greater by mass, the water phase including a nonionic surfactant having an HLB value of 14 or greater in an amount of 0.03 to 0.6% by mass is blended with pigments including an organic pigment, in an amount of 0.05 to 8% by mass.

(2) The high internal water phase water-in-oil emulsified cosmetic as described in (1), wherein the viscosity at the shear rate of 3.83 $sec^{-1}$ at 25° C. is 1 to 100 Pa·sec.

(3) The high internal water phase water-in-oil emulsified cosmetic as described in (1) or (2), wherein, at least, one nonionic surfactant having an HLB value of 14 or greater is selected from polyoxyalkylene alkyl ethers, polyglycerin fatty acid esters, polyoxyalkylene glycerin fatty acid esters and polyalkyleneglycol fatty acid esters.

(4) The high internal water phase water-in-oil emulsified cosmetic as described in any one of (1) to (3), wherein the cosmetic is a blusher cosmetic.

(5) A liquid applicator comprising a reservoir arranged in a barrel body, wherein a high internal water phase water-in-oil emulsified cosmetic as described in any one of (1) to (3) is stored in the reservoir.

(6) The liquid applicator as described in (5), comprising a structure formed of: an applying part fixed at the front end part of the barrel body for applying an application liquid by being put into contact with a target part; a thrusting mechanism arranged in the rear of the barrel body; a dispensing port for dispensing the application liquid to the applying part; and a communication passage formed to connect between the dispensing port and the reservoir, to push the application liquid from the reservoir to the dispensing port via the communication passage of the applying part by means of the thrusting mechanism and dispense the liquid from the dispensing port, wherein the applying part has a surface roughness Ra of 3 to 300 μm.

(7) The liquid applicator as described in (6), wherein the applying part includes a dispensing port plane having the dispensing port and an applying plane for applying the dispensed application liquid, and the dispensing port plane and the applying plane form two approximate flat planes having different angles of inclination.

(8) The liquid applicator as described in (7), wherein the applying plane is inclined with an angle of 0° to 90° with respect to the axis while the dispensing port plane is inclined with an angle of 10° to 45° relative to applying plane.

(9) The liquid applicator as described in any one of (6) to (8), wherein the applying part has a type A hardness of 60 or greater in accordance with JIS K6253-2006.

Effect of the Invention

The present invention can provide a high internal water phase water-in-oil emulsified cosmetic having water resistance, producing a fresh and light touch, being excellent in aging stability and brilliant in color available to such as a cream blusher. The invention can provide a liquid applicator, which dispenses an application liquid such as a liquid cosmetic, being viscous by nature, to an applying part so that the liquid can be directly applied to the skin and spread thinly thereon by patting without skill.

DETAILED DESCRIPTION OF THE PREFERRED EMBODIMENTS

Figure 1:
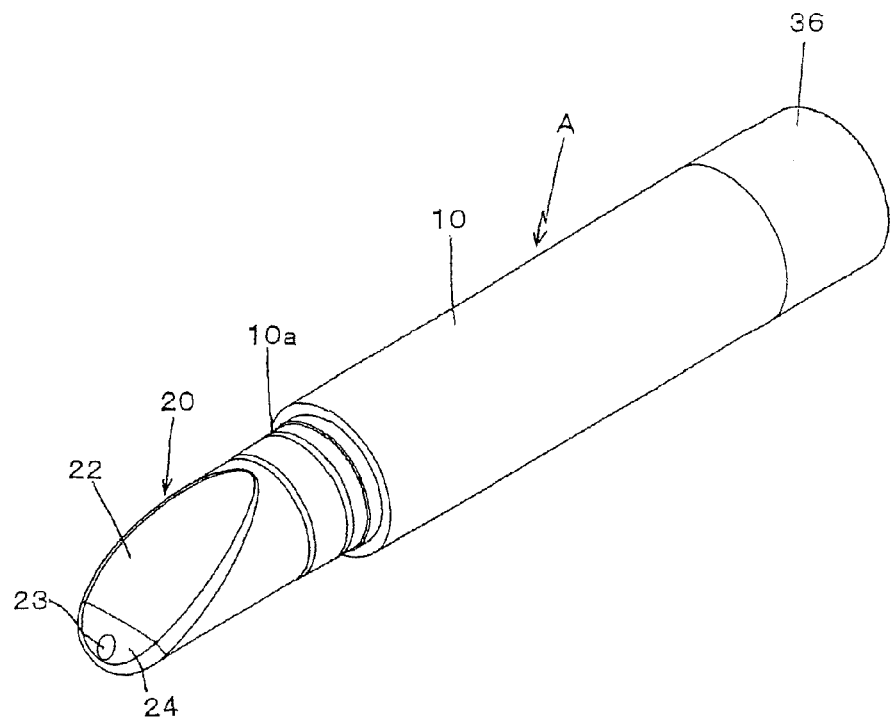
FIG. 1 is a perspective view showing one example of a liquid cosmetic applicator storing a high internal water phase water-in-oil emulsified cosmetic of the present invention.

Next, the embodiment of the present invention will be described in detail.

The high internal phase water-in-oil emulsified cosmetic of the present invention is characterized in that, in a system formed of an oil phase including silicone elastomer, polydimethylsiloxane and polyether modified silicone and a water phase including water in an amount of 60% or greater by mass, the water phase including a nonionic surfactant having an HLB value of 14 or greater in an amount of 0.03 to 0.6% by mass is blended with pigments including an organic pigment in an amount of 0.05 to 8% by mass, and the viscosity at the shear rate of 3.83 $sec^{-1}$ at 25° C. is 1 to 100 Pa·sec. Further, in order to stabilize the interface of each phase with the other, polyether modified silicone oil as a surfactant is blended on the oil phase side while at least one nonionic surfactant having an HLB value of 14 or greater, selected from polyoxyalkylene alkyl ethers, polyglycerin fatty acid esters, polyoxyalkylene glycerin fatty acid esters and polyoxyalkyleneglycol fatty acid esters, is blended on the water phase side. In particular, the nonionic surfactant having an HLB value of 14 or greater on the water phase side plays a role of stably dispersing pigments including an organic pigment into the water phase.

Here, the high internal water phase water-in-oil emulsified cosmetic of the present invention is an emulsified cosmetic of a water-in-oil type, W/O type, including a water content in an amount of 50% or greater by mass, preferably 60% or greater by mass, water being dispersed in the continuous oil phase.

Here, HLB is an indicator showing the hydrophilic-lipophilic balance, taking a value of 0 to 20. The closer to 0 an HLB is, the more lipophilic a surfactant is, and the closer to 20 an HLB is, the more hydrophilic a surfactant is. Various calculation methods have been known, or the values are also given in such as catalogs offered by the manufacturers. In the description of the present invention, the values given from the catalogs are used.

The pigments are used as coloring agents, and are not particularly limited. Usually, any pigment may be used as long as it can be used for the target part. For example, in a case of a cream blusher, red and orange colors are preferred, so that organic pigments such as Red No. 202, Red No. 226, Red No. 228, and Red No. 220 are usually used. Depending on cases, in order to adjust hue, such as Blue No. 404, blue No. 1 aluminum lake, and Yellow No. 4 aluminum lake may be used.

Other than the above, inorganic pigments such as titanium oxide, zinc oxide, Indian red, black iron oxides, yellow iron oxides, Prussian blue, and Ultramarine may be additionally used as the pigments blended on the water phase side. These pigments can be blended in such amounts not to degrade the effect of the present invention.

The content of the above pigments including organic pigments is preferably 0.05 to 8% by mass to the total amount of the cosmetic, or more preferably, 0.1 to 5% by mass (hereinbelow, % by mass will be written simply as %), in view of coloring performance, stability in the water phase. If the content of the organic pigments is less than 0.05%, satisfactory color cannot be obtained. On the other hand, the content exceeding 8% degrades dispersibility in the water phase and worsens the balance at the oil-water interface, bringing an unpreferable result.

Other than the pigments including organic pigments to be blended in the water phase, it is also possible to blend pigments that are readily blendable also on the oil phase side or that have been so treated. In this case, depending on the characteristics of the available pigments, or by differentiating the phase to which each pigment is blended, it is possible to blend the pigments, purposing the effect of multilayer formation and other effects. Examples include hydrophobic materials such as mica titanium, dye-coated mica titanium, metal-coated glass powder, titanium oxide-coated glass powder, titanium oxide-coated synthetic phlogopite, iron oxide/titanium oxide-coated synthetic phlogopite, argentine, bismuth oxychloride, aluminum powder, iron oxide-coated aluminum powder, polyethylene terephthalate-aluminum-epolxy resin laminate powder, polyethylene terephthalate-silver-epoxy resin laminate powder, polyethylene terephthalate-polyolefin laminate film powder, and polyethylene terephthalate-polymethyl methacrylate laminate film powder.

The content of these pigments blended on the oil phase side is preferably 0.05 to 5%, or more preferably 0.05 to 3% to the total amount of the cosmetic since the oil phase is relatively small in ratio compared to the water phase.

The nonionic surfactant used on the water phase side must enable to disperse stably these pigments blended on the water phase side. As the high internal water phase water-in-oil emulsified cosmetic, the surfactant is also demanded to include and stabilize a large amount of water inside the oil phase which is small in proportion so as to stably keep the water from separating. Further, in the water phase, salts are blended in order to gain emulsion stability. Since ionic surfactants degrade stability, nonionic surfactants are preferable. If the HLB value is low, the surfactant is oriented to the oil-water interface and the balance at the interface is hindered so that the stability lowers. Further, a low HLB value makes surfactant susceptible to the influence of salts. Therefore, the HLB value is specified to be 14 or greater, or preferably 15 or greater.

Listed as the examples of the nonionic surfactants are: polyoxyalkylene alkyl ethers including one or more alkylene groups selected from methylene, ethylene and propylene groups having 1 to 3 carbon atoms and a linear or branched long-chain alkyl group having 10 to 22 carbon atoms; polyglycerin fatty acid esters including a long-chain alkyl group having 10 to 22 carbon atoms; polyoxyalkylene glycerin fatty acid ethers including an alkylene group having 1 to 3 carbon atoms and a long-chain alkyl group having 10 to 22 carbon atoms; polyoxyalkyleneglycol fatty acid ethers including an alkylene group having 1 to 3 carbon atoms and a long-chain alkyl group having 10 to 22 carbon atoms; and the like. Specific examples of polyoxyalkylene alkyl ethers include such as polyoxyethylene lauryl ether, polyoxyethylene cetyl ether, polyoxyethylene stearyl ether, polyoxyethylene oleyl ether, polyoxyethylene behenyl ether, polyoxyethylene polyoxypropylene cetyl ether, and polyoxyethylene alkyl (12 to 14) ethers. Specific examples of polyglycerin fatty acid ethers include polyglyceryl laurate, polyglycerylmyristate, polyglycerylstearate. Specific examples of polyoxyalkylene glycerin fatty acid esters include polyoxyethylene glyceryl oleate. Specific examples of polyalkylene glycol fatty acid esters include polyethylene glycol monostearate and polyethylene glycol distearate. From these, one or more than one kinds can be used. Listed as the commercially available products can be BL-9EX, BL-21, BL-25, BC-15, BC-20, BC-23, BC-25, BC-30, BC-40, BS-20, BO-10V, BO-15V, BO-20V, BO-50V, BV-20, BB-30, BD-10, BT-12, PBC-34 (the above products are polyoxyalkylene alkyl ethers), Hexaglyn 1-L, Decaglyn 1-L, Decaglyn 1-M, Decaglyn 1-50SV (the above products are polyglycerin fatty acid esters), TMGO-15 (polyoxyalkylene glycerin fatty acid esters), MYS-25V, MYS-40V, MYS-40MV, MYS-45VM, MYS-45MV, MYS-55V, MYS-55MV, CDS-6000P (polyalkylene glycol fatty acid esters), (the above are manufactured by Nikko Chemicals Co., Ltd.), Emulgen 120, Emulgen 123P, Emulgen 130K, Emulgen 147, Emulgen 150, Emulgen 220, Emulgen 350, Emulgen 430, Emulgen 1118S-70, Emulgen 113 5S-70, Emulgen1150S-60, Emulgen 4085, Emulgen 2020G-HA, Emulgen 2025G (the above are polyoxyalkylene alkyl ethers, manufactured by Kao Corporation).

Since the above mentioned nonionic surfactants blended on the water phase are used to gain stability to the oil phase and pigments which are low in proportion, their content is preferably 1 to 60% relative to the pigments, 0.03 to 0.6%, or more preferably 0.05 to 0.5% relative to the total amount of the cosmetic. If the content of the nonionic surfactants is less than 0.03%, the balance at the oil-water interface as well as the dispersibility of the pigments degrades. On the other hand, if the content exceeds 0.6%, the feeling upon application degrades, resulting in being unpreferable.

The polyether modified silicone, as the surfactant blended on the oil phase side, makes smaller the particle size of the water phase to be dispersed in the continuous oil phase so as to change the touch when the cosmetic is applied and thereby improve impression of use. Further, the surfactant can be used as an emulsion stabilizer that disperses the water phase component which is large in proportion, in the form of minute particles so as to suppress aggregation of the water phase particles and enhance the stability over time as an emulsion. As the polyether modified silicone, polyoxyethylene-polydimethyl siloxane copolymer, polyethylene glycol-polydimethylsiloxyethyl dimethicone and others can be mentioned. As the commercially available polyoxyethylene-polydimethylsiloxane copolymer, silicone KF6011, KF6015 and KF6017 (manufactured by Shin-Etsu Chemical Co., Ltd.) can be mentioned. As the polyethylene glycol-polydimethylsiloxyethyl dimethicone, for example silicone KF 6028 (manufactured by Shin-Etsu Chemical Co., Ltd.) can be listed.

The content of the polyether modified silicone is preferably 0.5 to 5%, or more preferably 1 to 3%, relative to the total amount of the cosmetic.

The silicone elastomer to be blended on the oil phase side may be selected as appropriate in conformity with the aforementioned polyether modified silicone oil, and may use one or more kind of cross-linked polyorganosiloxanes. The silicone elastomer that can form stable gel using silicone oil as an oil agent is available. The silicone elastomer having silicone chains both in the main chain and the side chains, or the elastomer having silicone in the main chain and polyethers in the side chains in combination, and the like may be used. Further, using both of these can produce a high internal water phase water-in-oil emulsified composition with a high ratio of the internal water phase. As the commercially available products, silicone KSG 10 series and KSG21 series (manufactured by Shin-Etsu Chemical Co., Ltd.) can be listed.

The content of the silicone elastomer is preferably 0.1 to 6%, or more preferably 0.3 to 5%.

Polydimethylsiloxane to be blended on the oil phase side in the high internal water phase water-in-oil emulsified cosmetic, is an oil agent as the base of the oil phase forming the continuous phase in which the gel component consisting of the aforementioned silicone elastomer and polyether modified silicone is dispersed. Since the viscous oil agent gives an uncomfortable feeling when applied, the oil agent is preferably 1 to 20 mm$^2$/sec or more preferably 1.5 to 10 mm$^2$/sec at 25° C.

This polydimethylsiloxane may be used in a minimum necessary amount as the base so as to enable the gel component in the oil phase to disperse therein. The content is preferably 5 to 30% or more preferably 8 to 20% relative to the total amount of the cosmetic.

The high internal water phase water-in-oil emulsified cosmetic of the present invention can, of course, include aqueous components to be blended in a usual emulsified cosmetic in addition to the above-described essential components. For example, humectant, antiseptic, antioxidant, UV absorber, beauty ingredients, perfume, aroma retainer, thickener and others can be considered. These can be blended in a range that will not harm the effect of the present invention. The remaining part is adjusted with water such as purified water, and deionized water.

In the present invention, in view of precipitation control of pigments and application performance, the high internal water phase water-in-oil emulsified cosmetic is prepared so that its viscosity preferably falls within a range of 1 to 100 Pa·sec or more preferably 10 to 50 Pa·sec at a shear rate of 3.83 sec$^{-1}$ when measured by an EHD type viscometer at 25° C. using a standard cone rotor with a speed of 1 rpm.

When the viscosity is less than 1 Pa·sec, the water phase and the oil phase become liable to separate so that the aging stability degrades, resulting in being unpreferable. On the other hand, the viscosity exceeds 100 Pa·sec, the viscosity is so high that the application performance degrades, resulting in being unpreferable.

As has been described, since the high internal water phase water-in-oil emulsified cosmetic of the present invention in which pigments including organic pigments that have been dispersed by the nonionic surfactant having an HLB value of 14 or greater are blended in the water phase has a high internal water phase ratio, hence is characterized in that the emulsified particles collapse instantaneously when the cosmetic is applied, and the water of the internal phase spouts so that surplus moisture promptly evaporates or is absorbed and makes moist the skin without causing a sticky feeling, producing excellent impression of use. Since organic pigments are blended in this high internal water phase, the pigments smoothly and uniformly scatter and transfer to the skin as the cosmetic is applied while a coating protected by the oil phase as the continuous phase is formed on the skin surface. As a result, it becomes possible to provide water resistance and produce a fresh and light touch being brilliant in color and excellent in aging stability.

Further, as has been described heretofore, since it is not necessary to implement a surface treatment for stabilizing pigments including organic pigments at the time of blending, the problems in production causing cost increase, such as the need of washing the equipment and installation for surface treatment to prevent contamination or the need of provision of a separate apparatus, are solved, at the same time the usable pigments become less restrictive, so that it is possible to apply the high internal water phase water-in-oil emulsified cosmetic to wider kinds of cosmetics that need achievement of brilliant colors.

The high internal water phase water-in-oil emulsified cosmetic (which will be referred to hereinbelow as "emulsified cosmetic") of the present invention can be put to use with a liquid cosmetic applicator having an applying part.

The usable liquid cosmetic applicator is not particularly limited. An applicator including an applying part configured of an elastic material as an applying means and a container filled with the cosmetic can be considered.

Figure 2:
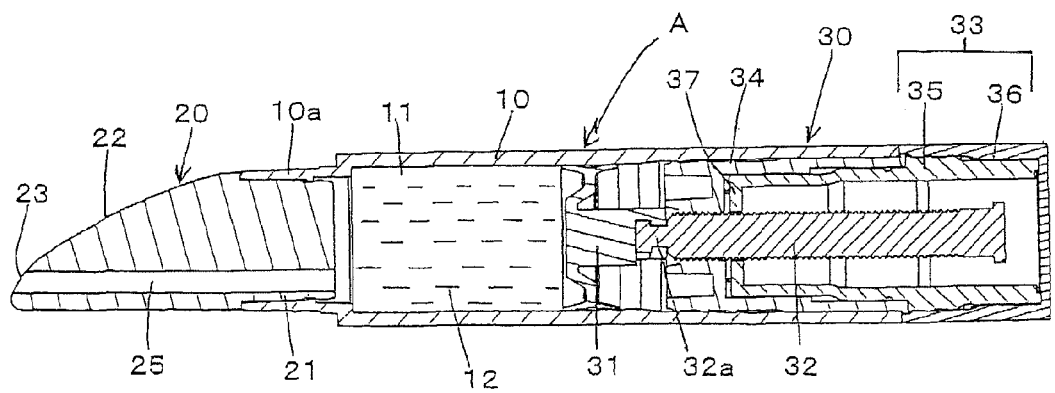
FIG. 2 is a vertical sectional view of the liquid cosmetic applicator shown in FIG. 1.
Figure 3A:
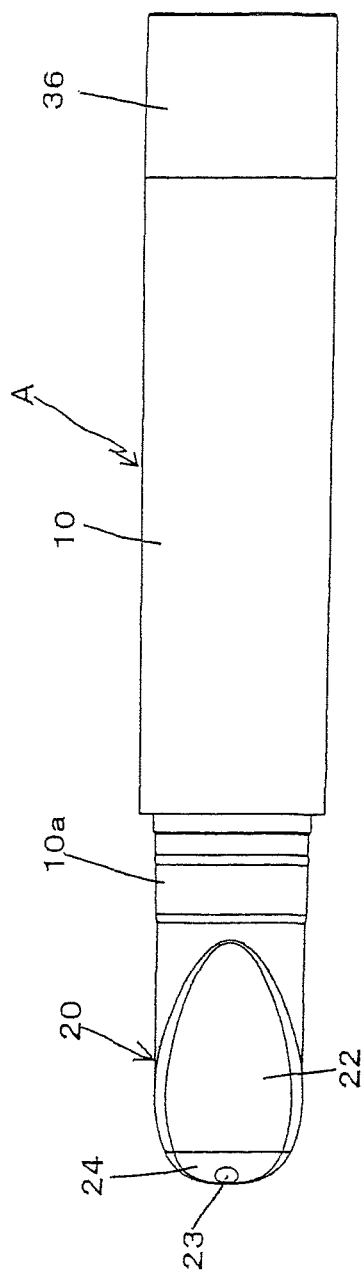
FIG. 3A is a plan view of the liquid cosmetic applicator shown in FIG. 1.
Figure 3B:
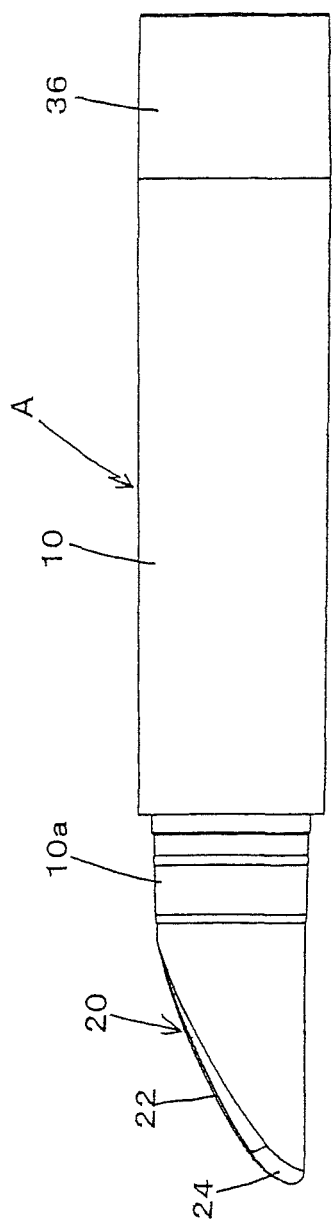
FIG. 3B is a front view of the liquid cosmetic applicator shown in FIG. 1.
Figure 3C:
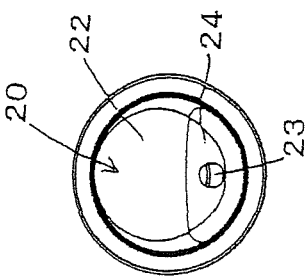
FIG. 3C is a left-side view of the liquid cosmetic applicator shown in FIG. 1.

Specifically, a liquid cosmetic applicator of a rotary propelling type dispenser, shown in FIGS. 1 to 3, which is excellent in usability, convenience and application performance, is preferable to use.

As shown in FIGS. 1 to 3, a liquid cosmetic applicator A of this type, includes: a reservoir 11 arranged inside a barrel body 10 for storing an application liquid 12 such as a cosmetic etc.; an applying part 20 fixed at a front end part 10a of barrel body 10 for applying application liquid 12 by its being put into contact with a target part such as the skin of the user; and a thrusting mechanism 30 arranged in the rear of barrel body 10 to dispense application liquid 12 such as a cosmetic stored in the reservoir 11 of barrel body 10 from a dispensing port 23 of applying part 20.

Barrel body 10 of this liquid cosmetic applicator A has an approximately hollow cylindrical configuration with its front end part 10a tapered. The outside diameter of the front end part 10a is formed approximately the same size with the inside diameter of a rear end part 21 of applying part 20. The rear end part 21 of applying part 20 is firmly joined to the front end part 10a by fitting. This joint is such that rear end part 21 of applying part 20 is fixed to front end part 10a by means of rib-like jagged parts that are formed on the opposing areas of front end part 10a and rear end part 21 and mate with each other.

The applying part 20 has a structure defined by an applying plane 22 that is a slope configuration formed by obliquely cutting the front end of the cylinder and a dispensing port plane 24 having a dispensing port 23 in front of the applying face, and is formed with a small-diametric communication passage 25 therein to establish communication with the dispensing port 23. In the present embodiment, as application liquid 12 is pressured by means of thrusting mechanism 30, the liquid passes through communication passage 25 and is dispensed from dispensing port 23 and stagnates on dispensing port plane 24.

The applying plane 22 that applies the ejected application liquid and the dispensing port plane 24 having dispensing port 23 form two approximate flat planes (slightly curved) having different angles of inclination. The applying plane 22 is preferably inclined with an angle of 0° to 90° with respect to the axis while the dispensing port plane 24 is preferably inclined with an angle of 10° to 45° relative to applying plane 22. Also, it is preferable that the intersection between applying plane 22 and dispensing port plane 24 forms a convex portion. In the present embodiment, applying plane 22 is inclined 25° with respect to the axis and dispensing port plane 24 is inclined 25° relative to applying plane 22 (50° relative to the axis). By this specification, the intersection between applying plane 22 and dispensing port plane 24 forms a convex portion so that the liquid in the dispensing port will not interfere upon application. Moreover, applying plane 22 forms a flat application surface when the liquid is applied to the skin surface, creating a large contact area with the target site part, thus improving application performance.

The size and the shape of the orifice and other factors of dispensing port 23 and communication passage 25 can be appropriately specified taking into consideration the viscosity, the blend composition and the mode of application. The shapes of the opening and hole of dispensing port 23 and communication passage 25 may have a circular, elliptic or other shape. The area of opening of dispensing port 23 is preferably 1 to 6 mm$^2$. In the present embodiment, dispensing port 23 has an elliptic shape having an area of 3.5 mm$^2$ and communication passage 25 is 30 mm in length with a diameter $\phi$ of 2 mm.

In liquid cosmetic applicator A of this type, in order to achieve preferable application performance and application liquid storage performance, applying part 20 is integrally formed of a polyolefin such as polyethylene (PE) and polypropylene (PP); a polyamide such as nylon; a polyester such as polyethylene terephthalate (PET) and polybutylene terephthalate (PBT); a resin material such as silicone resin and urethane resin; an elastomer such as a styrene elastomer, vinyl chloride elastomer, olefin elastomer, polyester elastomer, polyamide elastomer, and urethane elastomer; a rubber such as NBR, silicone rubber, EPDM, fluoro silicone rubber, fluoro rubber, urethane rubber, and natural rubber, and/or a composite of these. Applying part 20, preferably has a type A hardness of 60 or greater, or more preferably 70 or greater, in accordance with JIS K6253-2006, in order to enable fine application with uniform strength during application without causing any uneven loading pressure. This specification of the applying part having a type A hardness of 60 or greater makes it possible for the applying part to directly transfer and properly disperse the application force over the applied surface, hence apply the cosmetic more uniformly. In the present embodiment, applying part 20 is integrally formed of PP having a type A hardness of 90.

In order to enable preferable application of a viscous cosmetic or the like to the skin surface, application surface 22 of this applying part 20 is formed with a surface roughness Ra of 3 to 300 μm or preferably 20 to 80 μm so as to reduce friction with the skin surface and smoothen the application surface or form small irregularity.

In the present embodiment, from the viewpoint of reducing the resistance to the skin surface as the target of application, the angled edge of the periphery of applying plane 22 is trimmed. Further, the area of applying plane 22 can be appropriately designated taking into account the cosmetic type, viscosity, blend composition and the mode of application, and is preferably specified to be 100 to 400 mm$^2$. Further, the area of dispensing face 24 is designed so that the application liquid can well stagnate on dispensing port plane 24 and so that the liquid at the dispensing port will not interfere upon application, and is preferably 30 to 90 mm$^2$. In the present embodiment, the area of applying plane 22 was formed to be 210 mm$^2$ while the area of dispensing port plane 24 including dispensing port (having an area of 3.5 mm$^2$) was 60 mm$^2$.

The surface roughness of applying plane 22 is specified by arithmetic mean surface roughness Ra measured in accordance with JIS B0601:2001. In the present invention (including the examples described later), measurement of the surface roughness, arithmetic means surface roughness Ra, was carried out by using a laser microscope (VK-8500, manufactured by KEYENCE CORPORATION) set up with the smoothening conditions (filter size: 3×3, filter type: simple average, times of implementation: once) and a lens magnification of 10 times in color super depth-of-field mode. Other settings were set conforming to the standard specifications.

The surface roughness on applying plane 22 specified as above can be realized by forming irregularities with an arithmetic means surface roughness (Ra) of 3 μm to 300 μm, on the surface of the metal die for injection molding etc. that forms applying plane 22, or by implementing a secondary process (sandblasting with #60 sand) on the molding, and the like. The method of forming the irregularities may employ such as an etching process, an electrodischarge machining, and a sandblasting, on the surface of the metal die when a metal die is used as stated above. It is also possible to adopt a method of forming a metal die having minute irregularities on the surface thereof by using a foam metal or the like as the material of the die.

When the arithmetic mean surface roughness (Ra) is less than 3 μm, the poor surface roughness produces a furrow of the application liquid, causing uneven application. On the other hand, if the aforementioned value exceeds 300 μm, scratch traces form on the applied liquid surface. In the present embodiment, the arithmetic means surface roughness (Ra) of applying plane 22 was 30 μm.

Thrusting mechanism 30 is formed of a twist-up pushing type, and includes: a piston body 31 that moves forward and backward toward reservoir 11 inside the barrel body 10 so as to decrease and increase the volume of the reservoir space; and a driving mechanism (composed of such as a rotary actuator 33, a rod member 32, a fixed cylindrical part 34, and an inner cylindrical member 35), whereby the piston body 31, whose rear end is engaged with the front end, designated at 32a, of rod member 32 that is a thread rod, is advanced and retracted as the rod member 32 is rotated by the user so as to move forward and backward.

Piston body (gasket) 31 of this thrusting mechanism 30 is inserted from the rear end opening of barrel body 10 and arranged in a slidable manner to seal the interior wall of the middle part of the barrel body. As a result, the space enclosed between rear end part, designated at 21, of applying part 20 and piston body 31, inside barrel body 10 is formed as reservoir 11 of application liquid 12.

By user's rotational operation, the thrusting mechanism 30 slides its part, or the piston body 31 to seal the interior wall of the middle part of barrel body 10, so as to reduce and increase the volume of the reservoir 11 and thereby pressurize and depressurize application liquid 12. Thrusting mechanism 30 includes as its essential components, rotary actuator 33, rod member 32, fixed cylindrical part 34 (these correspond to the drive mechanism) and the aforementioned piston body 31.

Rotary actuator 33 is composed of inner cylindrical member 35 and an outer cylindrical cap 36 which are joined so as not to be rotatable to each other. The rotary actuator 33 as a whole is arranged rotatably relative to barrel body 10. Rod member 32 is slidable in the axial direction and fixed in the rotational direction with respect to this rotary actuator 33. This rotary actuator 33 is formed of outer cylindrical cap 36 and inner cylindrical member (also called "feeding part") 35, which are coupled so as not to be rotate relative to each other under normal conditions and so as to relatively rotate when applied with a rotational force over a fixed level. The entire rotary actuator 33 is arranged rotatably at the rear end of barrel body 10.

Fixed cylindrical part 34 that moves the aforementioned rod member 32 in and out is formed of an annular member and attached to barrel body 10 so as to be unable to rotate and move back and forth. A female thread is formed on the inner periphery of fixed cylindrical part 34 so as to mate with the male thread formed on the outer periphery of rod member 32. As rotary actuator 33 is rotated, rod member 32 rotates and moves back and forth by function of the male thread of rod member 32 mating with the female thread of fixed cylindrical part 34, whereby piston body 31 moves forward and backward.

The meshing portion, designated at 37, between fixed cylindrical part 34 and rotary actuator 33 (the outer peripheral surface in the front part of inner cylindrical member 35) forms a ratchet. Rotary actuator 33 is rotatable in both directions with respect to fixed cylindrical part 34 (barrel body 10 to which the part is fixed). When the actuator is rotated in the direction that dispenses the application liquid or the high-viscosity liquid cosmetic, the ratchet causes the fingers to feel a clicking touch as the liquid is dispensed. When the actuator is rotated in the other direction, the ratchet restrains rotation so that the actuator will rotate only when a rotational force greater than a set level is applied. That is, the ratchet has a structure providing a torque limiting function that releases the restraint and permits rotation when a rotational force greater than a preset level is applied in the other direction.

Also, the thrusting mechanism 30 retracts piston 31 as the aforementioned rotary actuator 33 is rotated in the other direction, to thereby provide a function of depressurizing application liquid 12 inside reservoir 11 of barrel body 10. With this function, it is possible for the thrusting mechanism 30 to depressurize application liquid 12, hence collect the liquid cosmetic into communication passage 25 formed in applying part 20 after thrusting mechanism 30 stops pressurizing application liquid 12. As another configuration, the aforementioned meshing portion 37 of rotary actuator 33 in thrusting mechanism 30 may be configured so as to completely lock the rotation in the other direction to thereby prohibit the liquid cosmetic from returning.

According to the thus configured liquid cosmetic applicator A storing the emulsion cosmetic of the present invention, it is possible to provide a liquid applicator, which can also be used with the high internal water phase water-in-oil emulsified cosmetic of the present invention such as a viscous blusher liquid etc., and which enables the emulsified cosmetic ejected from dispensing port 23 to be fed onto applying plane 22 so that the liquid can be readily applied and spread thin to the skin by patting without any skill. Further, in the present embodiment, the specifications of applying plane 22 having an inclination of 0° to 90° relative to the axis and the dispensing port plane 24 having an inclination of 10° to 45° relative to the applying plane and the intersection between applying plane 22 and dispensing port plane 24 forming a convex portion, make it possible for the application liquid to stably stagnate on dispensing port plane 24 and prevent the liquid at around the dispensing port from interfering upon application. Further, since applying part 20 including applying plane 22 has a type A hardness of 60 or greater based on JIS K6253-2006, the applying plane 22 offers a flat applying surface having a moderate hardness and a moderate surface roughness when applied on the skin surface. These properties of applying plane 22 provide favorable usability and excellent application performance for the applicators for viscous cosmetics, whereby the user can readily apply the application liquid to, and spread the liquid thin over, the skin by patting without any skill. Though, in the above description, the preferred mode of the liquid cosmetic applicator was described, the present invention should not be limited to the above configuration. Various changes and modifications can be made therein. For example, in the above configuration, the applicator uses a rotary propelling type dispensing container, but dispensing containers of a tube type, squeeze type, clicking type, aerosol type or other types may be used.

EXAMPLES

Next, the present invention will be described in further detail with reference to examples and comparative examples. However, the present invention should not be limited to the following and other examples.

Examples 1 to 4 and Comparative Examples 1 to 5

The oil phase part and the water phase part were separately prepared (the blending unit: % by mass, the total amount 100% by mass) according to the blending prescriptions shown in the following Table 1 and Table 2. The water phase part was gradually added while stirring the oil phase part intensely to obtain each high internal water phase water-in-oil emulsified cosmetic. The viscosity of the obtained high internal water phase water-in-oil emulsified cosmetics was measured by the following measurement method and the cosmetics were evaluated on aging stability, feeling upon application according to the following evaluation methods. The results are shown in Tables 1 and 2 below.

(Method of Measuring Viscosity)

For each of the prepared high internal water phase water-in-oil emulsified cosmetics, the viscosity at a temperature of 25° C. at a shear rate of 3.83 $\sec^{-1}$ was measured using a cone plate type viscometer (EHD type viscometer with the standard cone plate, manufactured by Toki Sangyo Co., Ltd.)

(Evaluation Method of Aging Stability)

Each of the prepared high internal water phase water-in-oil emulsified cosmetics had been kept at a 40° C. thermostatic chamber for one month, and the external appearance was visually observed. The aging stability was evaluated based on the following evaluation criteria.

Evaluation Criteria:

◯: there is no separation between the oil phase and the water phase, and no change is found compared to the state before the test;

Δ: some separation of the water phase is found; and,
X: The oil phase and the water phase have been separated.
(Evaluation Method of Feeling upon Application)

Ten female panelists having three or longer years of experience in making up actually use each of the prepared high internal water phase water-in-oil emulsified cosmetics. Impression of use upon application (sticky feeling, etc.) was evaluated based on the following evaluation criteria.

Evaluation Criteria:

○: the sample on which 8 or more panelists of 10 evaluated that impression of use was good;

Δ: the sample on which 4 to 7 panelists of 10 evaluated that the impression of use was good; and X: the sample on which only 3 or less panelists of 10 evaluated that impression of use was good.

TABLE 1

| | | | | | (Total Amount 100% by mass) Examples | | | |
|---|---|---|---|---|---|---|---|---|
| | | | | | 1 | 2 | 3 | 4 |
| Oil Phase | Gel Component | Gel | Silicone Elastomer | KSG-15*1 | 1 | 1 | 1 | 1 |
| | | | | KSG-210*2 | 3 | 3 | 3 | 3 |
| | | Surfactant | Polyether-modified Silicone | KF-6017*3 | 1.5 | 1.5 | 1.5 | 1.5 |
| | | | | KF-6028*4 | | | | |
| | | Thickener | Organic-modified Bentonite | | | | | |
| | | Oil Agent | Triehylhexanoin | | | | | |
| | Continuous Phase | Oil Agent | Polydimethyl Siloxane | KF-96 A-6cs*5 | 9.5 | 9.5 | 9.5 | 9.5 |
| | | | Volatile Silicone | KF-995*6 | | | | |
| | Pigment Phase | Oil Agent | | Cosmol 222*7 | | | | |
| | | Pigment | Pearl Pigment | Si01-MP-1005*8 | | 1 | | |
| Water Phase | Pigment Phase | Pigment | Organic Pigment | Red No. 226 | | 0.3 | | |
| | | | | Red No. 202 | 0.3 | | | |
| | | | | Red No. 228 | | | 0.3 | 0.3 |
| | | Surfactant | Nonionic | BB-30*9 | 0.06 | | | |
| | | | | BC-20*10 | | 0.06 | 0.06 | |
| | | | | BC-15*11 | | | | 0.06 |
| | | | | BC-10*12 | | | | |
| | Additive | Humectant | Butylene Glycol | | 8 | 8 | 8 | 8 |
| | | | Dipropylene Glycol | | | | | |
| | Other Common Additive Components*13 | | | | 6.5 | 6.5 | 6.5 | 6.5 |
| | Water (Purified Water) | | | | 70.14 | 69.14 | 70.14 | 70.14 |
| | HLB (when nonionic surfactant is used) | | | | 18 | 17 | 17 | 15.5 |
| Evaluation | Viscosity (25° C., Shear Rate = 3.83 sec$^{-1}$, Pa * sec) | | | | 20 | 30 | 22 | 21 |
| | Aging Stability | | | | ○ | ○ | ○ | ○ |
| | Feeling upon Application | | | | ○ | ○ | ○ | ○ |

TABLE 2

| | | | | | (Total Amount 100% by mass) Comparative Examples | | | | |
|---|---|---|---|---|---|---|---|---|---|
| | | | | | 1 | 2 | 3 | 4 | 5 |
| Oil Phase | Gel Component | Gel | Silicone Elastomer | KSG-15*1 | 1 | 1 | 1 | 5 | 1 |
| | | | | KSG-210*2 | 3 | 3 | 3 | 3.5 | 3 |
| | | Surfactant | Polyether-modified Silicone | KF-6017*3 | 1.5 | 1.5 | 1.5 | | 1.5 |
| | | | | KF-6028*4 | | | | 2 | |
| | | Thickener | Organic-modified Bentonite | | | | | 1.2 | |
| | | Oil Agent | Triehylhexanoin | | | | | 5 | |
| | Continuous Phase | Oil Agent | Polydimethyl Siloxane | KF-96 A-6cs*5 | 9.5 | 9.5 | 9.5 | 15.5 | 8.5 |
| | | | Volatile Silicone | KF-995*6 | | | | 23.1 | |
| | Pigment Phase | Oil Agent | | Cosmol222*7 | | | | | 1 |
| | | Pigment | Pearl Pigment | Si01-MP-1005*8 | | | | 1 | |
| Water Phase | Pigment Phase | Pigment | Organic Pigment | Red No. 226 | | 0.3 | | | 0.3*16 |
| | | | | Red No. 228 | 0.3 | | 0.3 | 0.3 | |
| | | Surfactant | Nonionic | BC-20*10 | | | | 0.6 | |
| | | | | BC-10*12 | 0.06 | | | | |
| | | Acrylic Resin | | AMPHOMER HC*14 | | 0.09 | | | |
| | | | | Luvimer100P*15 | | | 0.09 | | |
| | | Emulsion Stabilizer | | Aminomethyl Propanol | | 0.01 | 0.03 | | |
| | Addtive | Humectant | Butylene Glycol | | 8 | 8 | 8 | | 8 |
| | | | Dipropylene Glycol | | | | | 5 | |
| | Other Common Additive Components*13 | | | | 6.5 | 6.5 | 6.5 | 6.5 | 6.5 |

TABLE 2-continued

|  |  | (Total Amount 100% by mass) Comparative Examples | | | | |
|---|---|---|---|---|---|---|
|  |  | 1 | 2 | 3 | 4 | 5 |
|  | Water (Purified Water) | 70.1 | 70.08 | 70.14 | 36.8 | 70.2 |
|  | HLB (when nonionic surfactant is used) | 13.5 | — | — | 17 | — |
| Evaluation | Viscosity (25° C. Shear Rate = 3.83 sec$^{-1}$, Pa * sec) | 15 | — | — | 5 | 31 |
|  | Aging Stability | X | X | X | ○ | ○ |
|  | Feeling upon Application | ○ | X | X | X | Δ |

*[1] to *[16] in Table 1 and Table 2 above are as follows:-
*[1](dimethicone/vinyl dimethicone) crosspolymer/cyclopentasiloxane, manufactured by Shin-Etsu Chemical Co., Ltd.
*[2](dimethicone/(PEG-10/15) crosspolymer/dimethicone, manufactured by Shin-Etsu Chemical Co., Ltd.
*[3]PEG-10 dimethicone, manufactured by Shin-Etsu Chemical Co., Ltd.
*[4]PEG-9 polydimethyl-siloxy ethyl dimethicone, manufactured by Shin-Etsu Chemical Co., Ltd.
*[5]dimethicone with a viscosity of 6 mm$^2$/s at 25° C., manufactured by Shin-Etsu Chemical Co., Ltd.
*[6]cyclopentasiloxane, manufactured by Shin-Etsu Chemical Co., Ltd.
*[7]diisostearyl malate, manufactured by The Nisshin OiliO Group, Ltd.
*[8]silicone treated pearl pigment, manufactured by DAITO CHEMICAL CO., LTD.
*[9]polyoxyethylene behenyl ether, HLB = 18, manufactured by Nikko Chemicals Co., Ltd.
*[10]polyoxyethylene cetyl ether, HLB = 17, manufactured by Nikko Chemicals Co., Ltd.
*[11]polyoxyethylene cetyl ether, HLB = 15.5, manufactured by Nikko Chemicals Co., Ltd.
*[12]polyoxyethylene cetyl ether, HLB = 13.5, manufactured by Nikko Chemicals Co., Ltd.
*[13]common components: phenoxyethanol 0.5%, methyl paraben 0.2%, ethyl paraben 0.1% (the above as antiseptic substances), sodium citrate (anti-oxidant) 0.2%, sodium chloride 0.5%, ethanol 5%
*[14]octylacrylamide/acrylate ester copolymer, manufactured by Akzo Nobel
*[15]t-butyl acrylate/ethyl acrylate/methacrylic acid copolymer, a product of BASF
*[16]blended on the oil phase side when the phase oil is prepared As apparent from the results shown in Table 1 and Table 2 above, it was found out that the high internal water phase water-in-oil emulsified cosmetics of examples 1 to 4 falling within the scope of the present invention are more excellent in aging stability and application performance than those of comparative examples 1 to 5 falling out of the scope of the invention. It was also found as to the applicators that it is possible to provide a liquid applicator that is excellent in usability and application performance and that it is possible to deliver a proper amount of the water-in-oil emulsified cosmetic of each prescribed example, from the dispensing port to the applying part and hold the liquid therein, and the applying plane having the above-specified arithmetic means surface roughness (Ra) provides favorable usability and excellent application performance for the applicator which enables the user to readily apply the application liquid to, and spread the liquid thin over, the skin by patting without any skill.

Discussing the comparative examples individually, comparative example 1 is an example in which a nonionic surfactant having an HLB value less than the lower limit is used, and it was found that the aging stability is inferior. Comparative examples 2 and 3 are examples in which instead of a nonionic surfactant having an HLB value of 14 or greater, acrylic resin and aminomethyl propanol as an emulsion stabilizer is used, and it was found that the aging stability and feeling upon application are both inferior. Comparative example 4 is an example in which the content of the oil phase is increased, and it was found that stickiness increases and feeling upon application is inferior. Comparative example 5 is an example in which pigments are blended on the oil phase, and it was found that feeling upon application is somehow inferior though the content of the oil phase other than the pigments is prescribed the same as examples 1 to 4.

INDUSTRIAL APPLICABILITY

It is possible to produce high internal water phase water-in-oil emulsified cosmetics suitable for beauty products having brilliant colors, such as a blusher at low cost. Further, according to the liquid applicator suited to this cosmetic, a viscous cosmetic, for example, a cream blusher or other high internal water phase water-in-oil emulsified cosmetics can be applied and spread thin by patting the applying part on the skin without any skill, hence the applicator can be favorably used for foundation, lotion, skin care, etc.

LETTERS AND NUMERALS

A liquid cosmetic applicator
10 barrel body
11 application liquid reservoir
12 application liquid
20 applying part
22 applying plane
23 dispensing port
24 dispensing port plane
25 communication passage
30 thrusting mechanism
31 piston body
32 rod member
33 rotary actuator
34 fixed cylindrical part
35 inner cylindrical member
36 outer cylindrical cap

The invention claimed is:

1. A high internal water phase water-in-oil emulsified cosmetic, wherein in a system formed of an oil phase including 0.1 to 6% by mass of silicone elastomer, 5 to 30% by mass of polydimethylsiloxane, and 0.5 to 5% by mass of polyether modified silicone and a water phase including water in an amount of 60% or greater by mass, the water phase including a nonionic surfactant having an HLB value of 14 or greater in an amount of 0.03 to 0.6% by mass is blended with pigments including an organic pigment, in an amount of 0.05 to 8% by mass, and wherein the viscosity of the high internal water phase water-in-oil emulsified cosmetic at the shear rate of 3.83 sec$^{-1}$ at 25° C. is 1 to 100 Pa·sec.

2. The high internal water phase water-in-oil emulsified cosmetic as described in claim 1, wherein, at least, one nonionic surfactant having an HLB value of 14 or greater is selected from the group consisting of polyoxyalkylene alkyl ethers, polyglycerin fatty acid esters, polyoxyalkylene glycerin fatty acid esters and polyalkyleneglycol fatty acid esters.

3. The high internal water phase water-in-oil emulsified cosmetic as described in claim 1, wherein the cosmetic is a blusher cosmetic.

4. A liquid applicator comprising a reservoir arranged in a barrel body, wherein, a high internal water phase water-in-oil emulsified cosmetic according to as described in claim 1 is stored in the reservoir.

5. The liquid applicator as described in claim 4, comprising a structure formed of: an applying part fixed at the front end part of the barrel body for applying an application liquid by being put into contact with a target part; a thrusting mechanism arranged in the rear of the barrel body; a dispensing port for dispensing the application liquid to the applying part; and a communication passage formed to connect between the dispensing port and the reservoir, to push the application liquid from the reservoir to the dispensing port via the communication passage of the applying part by means of the thrusting mechanism and dispense the liquid from the dispensing port, wherein the applying part has a surface roughness Ra of 3 to 300 μm.

6. The liquid applicator as described in claim 5, wherein the applying part includes a dispensing port plane having the dispensing port and an applying plane for applying the dispensed application liquid, and the dispensing port plane and the applying plane form two approximate flat planes having different angles of inclination.

7. The liquid applicator as described in claim 6, wherein the applying plane is inclined with an angle of 0° to 90° with respect to the barrel body while the dispensing port plane is inclined with an angle of 10° to 45° relative to applying plane.

8. The liquid applicator as described in claim 5, wherein the applying part has a type A hardness of 60 or greater in accordance with JIS K6253-2006.

9. The high internal water phase water-in-oil emulsified cosmetic as described in claim 1, wherein the oil phase includes 1 to 5% by mass of polyether modified silicone.

* * * * *